(12) United States Patent
Hernandez et al.

(10) Patent No.: US 7,510,701 B2
(45) Date of Patent: Mar. 31, 2009

(54) AEROSOL-BASED INSECTICIDE COMPOSITIONS AND METHODS OF USING THE SAME

(75) Inventors: Ligia M. Hernandez, Kenner, LA (US); Anthony Haase, Loranger, LA (US)

(73) Assignee: Waterbury Companies, Inc., Waterbury, CT (US)

( * ) Notice: Subject to any disclaimer, the term of this patent is extended or adjusted under 35 U.S.C. 154(b) by 41 days.

(21) Appl. No.: 10/377,200

(22) Filed: Feb. 28, 2003

(65) Prior Publication Data

US 2004/0037782 A1 Feb. 26, 2004

Related U.S. Application Data

(63) Continuation-in-part of application No. 09/778,591, filed on Feb. 7, 2001, now abandoned.

(51) Int. Cl.
*A01N 25/06* (2006.01)
(52) U.S. Cl. .................. 424/45; 424/405; 424/406; 514/521; 514/531
(58) Field of Classification Search .................. 424/43, 424/45, 405, 406; 514/531, 521, 919
See application file for complete search history.

(56) References Cited

U.S. PATENT DOCUMENTS

| | | | |
|---|---|---|---|
| 4,316,914 A | 2/1982 | Coffee et al. | |
| 5,190,745 A | 3/1993 | Dohara et al. | |
| 5,396,730 A * | 3/1995 | VanGundy et al. | 43/131 |
| 5,707,638 A | 1/1998 | Losel et al. | |
| 5,773,016 A * | 6/1998 | Nelson | 424/405 |
| 5,872,143 A | 2/1999 | Tanaka et al. | |
| 6,124,466 A | 9/2000 | Matsuno et al. | |
| 6,159,956 A | 12/2000 | Barnes et al. | |
| 6,162,799 A | 12/2000 | Khambay et al. | |
| 6,506,396 B1 | 1/2003 | Narayanan et al. | |
| 6,706,760 B2 * | 3/2004 | Matsunaga | 514/531 |

FOREIGN PATENT DOCUMENTS

EP 0771526 A2 5/1997

OTHER PUBLICATIONS

Technical Data Sheet, Condea Vista Company, LPA Solvents, Apr. 1999.
Material Safety Data Sheet, Condea Vista Company, Vista LPA-210 Solvent, Aug. 2001.
Product Information Bulletin, Exxon, Isopar E Fluid, Nov. 1998.
Material Safety Data Sheet, AgrEvo Company, Delta Tech, Sep. 1998.
Formulator's Guide, AgrEvo Company, Delta Gard (deltamethrin), Oct. 1998.
Chemical Isomerization of Deltamethrin in Alcohol, Helmut Perschke and Manzoor Hussain, J. Agric. Food Chem. vol. 40, No. 4, 1992.
Material Safety Data Sheet, Aeropres Corporation, Aeropres 70, May 2002.
Code of Federal Regulations, Title 40, Chapter I, Part 180, Sec. 180.128, Jul. 2002.
Stepan, Product Bulletin, AMPHOSOL ® CG, Nov. 2000.
Stepan, Product Bulletin, STEOL ® 4N, Dec. 2001.
Stepan, Product Bulletin, NINOL ® 40-CO, Dec. 2001.
Stepan, Chemical Product & Company Identification, NINOL 40-CO, Jan. 2002.
Stepan, Chemical Product & Company Identification, STEOL 4N, Mar. 2002.
Stepan, Chemical Product & Company Identification, AMPHOSOL CG, Jul. 2002.
Material Safety Data Sheet, Exxon, Isopar E Fluid, Aug. 2000.
Farm Chemicals Handbook 99, vol. 85, pp. 310-311.
Material Safety Data Sheet, American Cyanamid Co., ALERT 2SC, Jun. 1997.
Material Safety Data Sheet, American Cyanamid Co., AC 303, 630 Technical, Jun. 1997.
Material Safety Data Sheet, American Cyanamid Co., AC 303, 630 2SC, Jun. 1997.
Phantom ® Termiticide, Physical and Chemical Data, BASF, 2000.

* cited by examiner

*Primary Examiner*—Neil Levy
(74) *Attorney, Agent, or Firm*—Carmody & Torrance LLP

(57) ABSTRACT

An aerosol-based insecticide composition comprising an active ingredient, such as deltamethrin, and a suitable carrier is disclosed as well as a method for its use. The insecticide composition may optionally contain one or more surfactants. Deltamethrin is preferably used as the active ingredient in the insecticide composition because of its tolerance for use on food. Furthermore, it has also been determined that deltamethrin is non-repellant to termites.

12 Claims, No Drawings

AEROSOL-BASED INSECTICIDE COMPOSITIONS AND METHODS OF USING THE SAME

CROSS REFERENCE TO RELATED APPLICATIONS

This application is a continuation-in-part of application Ser. No. 09/778,591, filed Feb. 7, 2001, now abandoned which is herein incorporated by reference in its entirety, now pending.

FIELD OF THE INVENTION

This invention relates to novel chemical insecticide formulations that having a recognized tolerance of the active ingredients for use in food and methods for preparing and using said formulation. In particular, this invention is directed to a novel insecticide formulation that is suited for aerosol-based applications, including aerosolized foam applications.

BACKGROUND OF THE INVENTION

Insecticides generally refer to a wide range of environmental interventions that have as their objective, the reduction of insect pests to an acceptable level from a particular area. Specific control techniques include chemical, physical and biological mechanisms, however, this invention is directed towards chemical insecticides.

The great majority of insecticides used today comprise synthetic compounds that affect the nervous system of insects on contact. Historically, chlorinated hydrocarbons such as DDT, chlordane and toxaphene had been used, but many of these compounds have been banned in the U.S. or fallen out of favor. Organophosphates, such as malathion, parathion, and dimethoate are currently widely used active ingredients for insecticides. A wide range of biological insecticides are also in use today. Although insecticides are widely used and provide great benefits to the users, environmental and social costs of widespread use can be high. For example, the use of DDT has been banned in the U.S. since 1973 because of its long-range environmental and human safety impacts, despite the fact that it functioned well as an insecticide.

A variety of insecticide formulations are known. For example, U.S. Pat. No. 6,159,956 discusses the preparation and use of difluorovinylsilane as an insecticide. Likewise, U.S. Pat. No. 6,162,799 discusses the preparation and use of certain naphthoquinone derivatives as pesticides and U.S. Pat. No. 6,124,466 promotes the use of certain nitroisourea derivatives for their insecticidal activity.

In formulating insecticides, a variety of considerations need to be weighed. First, obviously, one must utilize an active ingredient, or ingredients, that possess the appropriate degree of insecticidal activity towards the group of insects it is intended to be used against. However, the active ingredient must be such that it is safe for human use and reasonably environmentally safe, when being applied according to its instructions. One means of ensuring that the active ingredient is safe for human use is to use an active ingredient(s) that has a recognized tolerance for use on food, thus allowing for use in food preparation areas. Preferably, the active ingredient(s) is susceptible to being naturally degraded by organisms in the soil, or otherwise, upon extended exposure to the environment.

Typically, the active ingredient(s) in an insecticide formulation are soulblized or dispersed in a carrier, which will generally make up the bulk of the formulation. A variety of carrier characteristics, such as solubility or dispersability of the active ingredient in the carrier, toxicity of the carrier, odor, volatile organic content, biodegradability, and flammability, need to be considered in the choice of an effective carrier. Preferably the active ingredient(s) will be dissolved by, or dispersed in, the carrier during storage so that no mixing is required just prior to use. Carrier choice can also be limited by the need to aerosolize or foam the insecticide. Frequently there are trade-offs among these characteristics in choosing the most effective overall carrier.

Most preferably, the carrier(s) can dissolve the active ingredient(s) into an insecticide formulation that achieves the appropriate level of insecticidal activity, while at the same time posing little or no danger to human health and the environment when used as intended. The formulation should also possess low odor, have low volatile organic content, be biodegradable and relatively non-flammable.

It is also desired that the active ingredient in the insecticide composition is non-repellant to termites. By "non-repellant" what is meant is that the termites do not detect the active ingredient and will readily move through the treated zone, picking up a lethal dose of the active ingredient.

SUMMARY OF THE INVENTION

The inventors herein have discovered an insecticide formulation comprising:
(a) an active ingredient having a tolerance for use on food or in a food preparation area; and
(b) a suitable carrier;
wherein the insecticide formulation containing an effective amount of an aerosol propellant that is compatible with the insecticide formulation and optionally, one or more foaming agents.

The insecticide compositions of the invention can provide an effective insecticide that has low volatile organic content and odor.

DETAILED DESCRIPTION OF THE INVENTION

The inventors herein have discovered that effective insecticides can be formulated which promote most advantages typically sought in insecticides. In particular, the insecticide formulations of this invention provide an excellent level of insecticidal activity, while, at the same time, posing low levels of risk to human safety and the environment when used as directed. Furthermore, the active ingredient(s) in the insecticide formulations have a tolerance allowing for their use on food and in food preparation areas. In addition, the formulations have low levels of objectionable odors, low volatile organic content and low flammability.

The insecticide formulations of the instant invention can be dispersed in an appropriate carrier and used in aerosol applications. In an alternate embodiment, the insecticide formulation further comprises one or more foaming agents (surfactants). Depending on the particular application, different solvents and/or aerosols may be used. When used in an aerosol application not containing foaming agent(s) of the invention, compositions of the invention can be used without the need for mixing directly prior to use. However, aerosol formulations containing the foaming agents do require mixing (i.e., shaking) immediately prior to use. In addition, if the formulations containing foaming agents are used for an extended time, they may require additional mixing at periodic intervals during use.

These and other objects can be accomplished by formulating an insecticide comprising:
(a) an active ingredient having a tolerance for use on food or in a food preparation area; and
(b) a suitable carrier;
wherein the insecticide formulation containing an effective amount of an aerosol propellant that is compatible with the insecticide formulation and optionally, one or more foaming agents.

Pyrethrins, and in particular deltamethrin, an α-cyano-pyrethroid, are the preferred active ingredients of the insecticide formulation of this invention and provides the formulation with its insecticidal activity. The International Union of Pure and Applied Chemistry name for Deltamethrin is (S)-α-cyano-3-phenoxybenzyl (1R)-cis-3-(2,2-dibromovinyl)-2,2-dimethylcyclopropane-carboxylate. Deltamethrin is produced by AgrEvo Environmental Health of 95 Chestnut Ridge Road, Montvale, N.J., 07645. The concentration of deltamethrin in the insecticide formulation may range from 0.01 to 2% by weight of the insecticide without propellant, but is preferably from 0.01 to 0.5% by weight of the insecticide without propellant and most preferably from 0.10 to 0.30% by weight of the insecticide without the propellant. Surprisingly, the inventors have discovered that deltamethrin is non-repellant to termites, meaning that termites do not detect the deltamethrin in the treated area and will readily move through the treated area, picking up a lethal dose of the deltamethrin.

One of the objects of the invention is to create an insecticide formulation that can be used in food handling establishments where food is prepared. A benefit of using deltamethrin (or another similar pyrethrin) is that it has a tolerance allowing for its use on food or in a food preparation area. A list of active ingredient that have a tolerance allowing for their use on foods and in food preparation areas is codified at 40 C.F.R. Part 180. The tolerance of pyrethrins in food, including deltamethrin, is codified specifically at 40 C.F.R. 180.128.

In addition to the deltamethrin, the insecticides of this invention may also comprise additional active ingredients that are certified as usable in a food environment. Such active ingredients include, for example, Pyrethrins and Piperonyl Butoxide. Both of the foregoing are available from Prentiss, Inc. of Rowell, Ga. If used, the concentration of these additional active ingredients in the insecticide may preferably range from 0.05 to 1.0 percent by weight of the insecticide without propellant.

When the insecticide formulation does not contain foaming agent(s), the preferred carrier for use in the invention is an iso-paraffinic hydrocarbon carrier. The concentration of aromatic hydrocarbons in the carrier is desirably less than 1% by weight, preferably less than 0.5% by weight and most preferably less than 0.1% by weight.

The iso-paraffinic hydrocarbon carrier is a blend of aliphatic hydrocarbons, preferably branched, with the general empirical formula of $C_nH_{2n+2}$. Preferably, the hydrocarbon carrier comprises a mixture of $C_8$ and $C_9$ branched iso-paraffinic hydrocarbons. The concentration of aromatic hydrocarbons in the carrier is desirably less than 1% by weight, preferably less than 0.5% by weight and most preferably less than 0.1% by weight. Preferably, the concentration of non-aromatic compounds with carbon-carbon double bonds, such as alkenes, cycloalkenes, dienes and cyclodienes, is less than about 2% by weight of the carrier, most preferably, less than about 1% by weight of the carrier. Particularly, preferred iso-paraffinic hydrocarbons are sold under the tradename ISOPAR® by the Exxon Chemical Company, P.O. Box 3272, Houston, Tex. 77253-3272. A particularly preferred ISOPAR® solvent, ISOPAR E®, is a mixture of $C_8$ and $C_9$ branched iso-paraffinic hydrocarbons. Other iso-paraffinic solvents are sold by the Condea Vista Company of Houston, Tex. under the tradename, VISTA LPA®. These solvents contain iso-paraffins, but also contain higher concentrations of other paraffins and naphthenic hydrocarbons (as used herein naphthenic hydrocarbons means cyclic hydrocarbons that are not aromatic in nature such as cyclohexane). A combination of the ISOPAR® and VISTA LPA® solvents produces an insecticide that effectively dissolves the deltamethrin with relatively low volatile organic content.

The concentration of iso-paraffinic carrier in the insecticide formulation may range from about 80% to 99.98% by weight of the insecticide without propellant, but preferably ranges from about 97% to 99.98% by weight of the insecticide without propellant and most preferably the insecticide comprises substantially only the deltamethrin, the iso-paraffinic carrier, and if desired the aerosol propellant. As noted the iso-paraffinic carrier may preferably comprise a mixture of iso-paraffinic solvents with the total concentration of the mixture within the foregoing concentration parameters. The iso-paraffinic carrier of this invention acts as an excellent solvent for deltamethrin as well as the optional additional active ingredients listed above. It is believed that one of the reasons these formulations have been found to be non-repellant to termites is because the unique linear evaporation-rate properties of Isopar E promote an even dispersion of solute residue on surfaces, rather than recrystalization into larger more easily detectable particles.

The deltamethrin is dissolved in the iso-paraffinic hydrocarbon carrier with mixing. Once effectively mixed with the iso-paraffinic hydrocarbon carrier, the deltamethrin will generally remain in solution and no further mixing or shaking of the product will be required. Some iso-paraffinic hydrocarbon carrier formulations of the invention may require heat in order to effectively dissolve the deltamethrin. However, other iso-paraffinic hydrocarbon carrier formulations of the invention can effectively dissolve the deltamethrin without heat. Once dissolved, the deltamethrin/carrier combination can be charged into an empty aerosol can, the valve installed, and the aerosol propellant added.

When the insecticide formulation further comprises one or more foaming agents, the preferred carrier is deionized water rather than an iso-paraffinic hydrocarbon carrier. In this instance, the concentration of the deionized water is 55% to 75% by weight of the insecticide composition, preferably 60% to 70% by weight of the insecticide composition.

Foaming agents that may be usable in formulations of the invention include sodium laureth sulfate, cocamide DEA, and cocamidopropyl betaine. Preferably the sodium laureth sulfate, cocamide diethanol amide, and cocamidopropyl betaine are used in combination. Most preferably the foaming agent of the invention consists of 10 percent by weight cocamide DEA, 50 percent by weight sodium laureth sulfate, and 40 percent by weight cocamidopropyl betaine. The concentration of the foaming agent(s) in the insecticide composition is 10% to 25% by weight, more preferably 15% to 20% by weight of the composition.

A suitable source of sodium laureth sulfate is available from Stepan Company under the tradename Steol® 4N. A suitable source of cocamide DEA is available from Stepan Company under the tradename Ninol® 40-CO. A suitable source of cocamidopropyl betaine is available from Stepan Company under the trade name Amphosol® CG.

The aerosol insecticide formulations of the invention are compatible with a variety of aerosol propellants. When the formulations do not contain the one or more surfactants, the inventors have found carbon dioxide, liquefied petroleum gasses, hydrofluorocarbons, and known chlorofluorocarbon replacements to be particularly useful aerosol propellants. One skilled in the art would know that the amount of aerosol propellant usable in the composition depends on the particular aerosol propellant being used.

When surfactants are used in insecticide formulations of the invention, the propellant preferably comprises a hydrocarbon propellant containing, for example, a mixture of propane and isobutene. Other suitable hydrocarbon propellants would also be known to one skilled in the art. One suitable propellant is available from Aeropres Corporation under the tradename Aeropres 70 (A-70), and is formulated to reach 70 pounds of pressure at room temperature. The concentration of the propellant in the insecticide formulation containing surfactants is approximately 10-20% by weight of the composition.

The insecticides of this invention may be applied in the form of an aerosol spray or as an aerosolized foam. The insecticides are effective against a variety of insects including ants, roaches, flies, spiders and similar insects, while at the same time having a tolerance allowing for their use on food and in food preparation areas. Furthermore, the insecticide formulations are non-repellant to termites.

Advantageously, because of the solubilizing power of the iso-paraffinic hydrocarbon carrier for the deltamethrin, the aerosol insecticide formulation not containing foaming agent(s) may be applied without mixing or shaking immediately prior to the application. As discussed above, insecticide formulations containing foaming agent(s) do need to be mixed by shaking immediately prior to application.

This invention is further demonstrated by the following examples, which should be taken as illustrative and not limiting in any manner.

EXAMPLE I 0.5 grams of deltamethrin were dissolved with stirring into 359.5 grams of ISOPAR® E solvent. The mixture was stirred at room temperature, until the deltamethrin was dissolved. The mixture was added to an aerosol can, a valve installed, and 540.0 grams of liquefied petroleum gas (aerosol propellant) were added. The insecticide was stored in the aerosol can for several months and remained a uniformly mixed effective insecticide.

EXAMPLE II 121.0 grams of VISTA LPA-210® solvent were heated to 120° F. and 0.5 grams of deltamethrin was added to the solvent with mixing until dissolved. 175.5 grams of ISOPAR-E® solvent was added with stirring. The mixture was added to an aerosol can, a valve installed, and 603.0 grams of liquefied petroleum gas (aerosol propellant) were added. The insecticide was stored in the aerosol can for several months and remained a uniformly mixed effective insecticide.

EXAMPLE III 923.0 grams of VISTA LPA-210® solvent were heated to 120° F. and 1.0 gram of deltamethrin was added to the solvent with mixing until dissolved. 660.0 grams of ISOPAR-E® solvent was added with stirring. The mixture was added to an aerosol can, a valve installed, and 66.0 grams of carbon dioxide (aerosol propellant) were added. The insecticide was stored in the aerosol can for several months and remained a uniformly mixed effective insecticide.

EXAMPLE IV 1119.0 grams of deionized water were heated to 180° F. and 0.96 grams of deltamethrin were added to the water with stirring for about 30 minutes, until dissolved. After the deltamethrin was dissolved, 120 grams of sodium laureth sulfate, 24 grams of cocamide DEA and 96 grams of cocamidopropyl betaine were added to the mixture until well mixed. The mixture was added to an aerosol can, a valve installed, and 240 grams of A-70™ (aerosol propellant) were added. The insecticide was stored in the aerosol can. The insecticide required shaking immediately prior to use. If the insecticide is used for an extended period of time, it may also be necessary to shake the insecticide formulation at various intervals during use.

One of the major advantages of the foaming aerosol-based insecticide compositions of the invention is that the formulations are do not require separate mixing steps prior to use. Unlike many of the foaming insecticide compositions of the prior art which required additional processing steps to first mix the foaming agent(s) together and to then mix the foaming agent(s) into the remaining ingredients of the composition prior to use, the foaming insecticide compositions of the present invention are ready to use, and only require shaking of the insecticide compositions immediately prior to use.

What is claimed is:

1. A method of exterminating termites in a food preparation area, which method comprises treating surfaces in a food preparation area with an aerosol spray of an insecticide composition, wherein the insecticide composition consists essentially of:
   a) 0.01 to 2.0 percent by weight of an active ingredient based on the total weight of the insecticide composition, wherein the active ingredient has a tolerance that allows for its use on food and in food preparation areas; and
   b) 97 to 99.98 percent by weight of a branched aliphatic hydrocarbon carrier comprising a mixture of C8 and C9 branched isoparaffins and having a general empirical formula of $C_nH_{2n+2}$, based on the total weight of the insecticide composition;
   wherein said insecticide composition is charged to an empty aerosol can and an effective amount of an aerosol propellant that is compatible with the insecticide composition is added to said can,
   wherein the active ingredient comprises a pyrethrin; and
   whereby termites moving through the treated area will be exterminated.

2. The method of claim 1, wherein said pyrethrin comprises deltamethrin.

3. The method of claim 2, wherein the insecticide composition is non-repellant to termites.

4. The method of claim 2, wherein the deltamethrin has a concentration of 0.01 to 0.5 percent by weight based on the total weight of the insecticide composition.

5. The method of claim 4, wherein the deltamethrin has a concentration of 0.1 to 0.3 percent by weight based on the total weight of the insecticide composition.

6. The method of claim 1, wherein the concentration of aromatic hydrocarbons in the carrier is less than 1 percent by weight of the carrier.

7. The method of claim 1, wherein the aerosol propellant is selected from the group consisting of carbon dioxide and liquefied petroleum gas.

8. The method of claim 1, wherein the insecticide composition comprises an additional active ingredient selected from the group consisting of pyrethrins and piperonyl butoxide, wherein said additional active ingredient has a tolerance allowing for its use on food and in food preparation areas.

9. The method of claim 8, wherein the additional active ingredient is piperonyl butoxide.

10. A method of exterminating termites in a food preparation area, which method comprises treating surfaces in a food preparation area with an aerosol spray of an insecticide composition, wherein the insecticide composition consists essentially of:
  i) 0.01 to 2.0 percent by weight of deltarnethrin based on the total weight of the insecticide composition;
  ii) 0.05 to 1.0 percent by weight of an active ingredient based on the total weight of the insecticide composition, wherein the active ingredient is selected from the group consisting of pyrethrins and piperonyl butoxide, and wherein the active ingredient has a tolerance that allows for its use on food and in food preparation areas; and
  iii) 97 to 99.98 percent by weight of a branched aliphatic hydrocarbon carrier comprising a mixture of C8 and C9 branched isoparaffins and having a general empirical formula of $C_nH_{2n+2}$ based on the total weight of the insecticide;
  wherein said insecticide composition is charged to an empty aerosol can and an effective amount of an aerosol propellant that is compatible with the insecticide composition is added to said can; and
  whereby termites moving through the treated area will be exterminated.

11. The method of claim 10, wherein the insecticide composition is non-repellant to termites.

12. A method of exterminating termites utilizing an insecticide composition consisting essentially of (a) 0.01 to 2.0 percent by weight of an active ingredient based on the total weight of the insecticide composition, wherein the active ingredient has a tolerance that allows for its use on food and in food preparation areas, and (b) 97 to 99.98 percent by weight of a branched aliphatic hydrocarbon carrier comprising a mixture of C8 and C9 branched isoparaffins and having a general empirical formula of $C_nH_{2n+2}$, based on the total weight of the insecticide composition, wherein said insecticide composition is charged to an empty aerosol can and an effective amount of an aerosol propellant that is compatible with the insecticide composition is added to said can and wherein the active ingredient comprises a pyretbrin; wherein the method of exterminating comprises the steps of:
  treating a surface in a food preparation area, prior to contact between the termites and the surface, with an aerosol spray having said insecticide composition; and
  permitting the termites to contact the insecticide composition on the surface;
  whereby termites coming into contact with the insecticide composition will be exterminated.

* * * * *